United States Patent
Zickler

(10) Patent No.: US 7,811,280 B2
(45) Date of Patent: Oct. 12, 2010

(54) SYSTEM AND METHOD FOR LASER ABLATION CALIBRATION

(75) Inventor: Leander Zickler, Menlo Park, CA (US)

(73) Assignee: AMO Manufacturing USA, LLC., Santa Ana, CA (US)

( * ) Notice: Subject to any disclaimer, the term of this patent is extended or adjusted under 35 U.S.C. 154(b) by 675 days.

(21) Appl. No.: 11/341,917

(22) Filed: Jan. 26, 2006

(65) Prior Publication Data

US 2007/0173797 A1 Jul. 26, 2007

(51) Int. Cl.
A61B 18/18 (2006.01)
(52) U.S. Cl. .............................. 606/10; 128/898; 606/4; 356/450
(58) Field of Classification Search ................ 356/450, 356/496, 503–505, 468; 606/4–6, 10–12, 606/17, 107, 166; 607/89; 128/898
See application file for complete search history.

(56) References Cited

U.S. PATENT DOCUMENTS

| | | | |
|---|---|---|---|
| 4,665,913 A | 5/1987 | L'Esperance, Jr. | |
| 4,669,466 A | 6/1987 | L'Esperance | |
| 4,732,148 A | 3/1988 | L'Esperance, Jr. | |
| 4,770,172 A | 9/1988 | L'Esperance, Jr. | |
| 4,773,414 A | 9/1988 | L'Esperance, Jr. | |
| 4,777,637 A * | 10/1988 | Hayashi et al. | 372/46.012 |
| 5,108,388 A | 4/1992 | Trokel | |
| 5,144,630 A | 9/1992 | Lin | |
| 5,163,934 A | 11/1992 | Munnerlyn | |
| 5,196,006 A * | 3/1993 | Klopotek et al. | 606/32 |
| 5,207,668 A | 5/1993 | L'Esperance, Jr. | |
| 5,219,343 A | 6/1993 | L'Esperance, Jr. | |
| 5,323,229 A * | 6/1994 | May et al. | 356/479 |
| 5,520,679 A | 5/1996 | Lin | |
| 5,556,395 A | 9/1996 | Shimmick et al. | |
| 5,624,436 A | 4/1997 | Nakamura et al. | |
| 5,630,810 A * | 5/1997 | Machat | 606/5 |
| 5,646,791 A | 7/1997 | Glockler | |
| 5,742,626 A | 4/1998 | Mead et al. | |
| 5,772,656 A * | 6/1998 | Klopotek | 606/12 |
| 5,782,822 A | 7/1998 | Telfair et al. | |
| 6,008,904 A * | 12/1999 | Ishii et al. | 356/512 |
| 6,080,144 A | 6/2000 | O'Donnell, Jr. | |

(Continued)

FOREIGN PATENT DOCUMENTS

WO    WO 99/04220 A    1/1999

(Continued)

*Primary Examiner*—Henry M Johnson, III
*Assistant Examiner*—Aisha Hunte

(57) ABSTRACT

Systems and method for determining ablation beam characteristics are provided. Methods include ablating an article with the ablation beam to form a test location having an ablation depth, transmitting a first beam through the test location of the article, transmitting a second beam through a reference location, and determining an ablation beam characteristic based on a phase relationship of the first beam and the second beam downstream of the article. Systems include a light source assembly transmitting a first beam through an ablated test location of an article and a second beam through a reference location disposed outside of the test location, a sensor assembly detecting a first beam and second beam superimposition downstream of the article, and a phase relationship code module for determining a phase relationship between the first beam and the second beam, based on the first beam and second beam superimposition.

19 Claims, 7 Drawing Sheets

U.S. PATENT DOCUMENTS

| | | | |
|---|---|---|---|
| 6,090,102 | A | 7/2000 | Telfair et al. |
| 6,116,737 | A | 9/2000 | Kern |
| 6,195,164 | B1 | 2/2001 | Thompson |
| 6,245,058 | B1 | 6/2001 | Suzuki |
| 6,245,059 | B1 * | 6/2001 | Clapham ................. 606/5 |
| 6,251,101 | B1 | 6/2001 | Glockler |
| 6,268,921 | B1 | 7/2001 | Seitz et al. |
| 6,271,914 | B1 * | 8/2001 | Frey et al. ............ 356/124 |
| 6,322,216 | B1 | 11/2001 | Yee et al. |
| 6,322,555 | B1 | 11/2001 | LaHaye |
| 6,331,177 | B1 | 12/2001 | Munnerlyn et al. |
| 6,369,898 | B1 | 4/2002 | Van Saarloos et al. |
| 6,392,756 | B1 * | 5/2002 | Li et al. ............... 356/632 |
| 6,454,761 | B1 * | 9/2002 | Freedman ............... 606/5 |
| 6,559,934 | B1 | 5/2003 | Yee et al. |
| 6,562,026 | B2 | 5/2003 | Glockler |
| 6,666,855 | B2 | 12/2003 | Somani et al. |
| 6,816,316 | B2 | 11/2004 | Caudle et al. |
| 6,817,998 | B2 | 11/2004 | LaHaye |
| 7,001,375 | B2 | 2/2006 | Yee et al. |
| 7,001,376 | B2 | 2/2006 | Somani et al. |
| 7,196,800 | B1 * | 3/2007 | Birdsley et al. ............ 356/505 |
| 7,238,177 | B2 | 7/2007 | Somani et al. |
| 2002/0026181 | A1 | 2/2002 | O'Donnell, Jr. |
| 2003/0107742 | A1 * | 6/2003 | Tualle ................. 356/450 |
| 2004/0102764 | A1 * | 5/2004 | Balling ................. 606/5 |
| 2005/0094249 | A1 | 5/2005 | Imajuku et al. |
| 2005/0094262 | A1 | 5/2005 | Spediacci et al. |
| 2005/0122572 | A1 * | 6/2005 | Campbell et al. ...... 359/337.22 |
| 2007/0173792 | A1 | 7/2007 | Arnoldussen |

FOREIGN PATENT DOCUMENTS

| | | |
|---|---|---|
| WO | WO 00/41639 A | 7/2000 |
| WO | WO 02/076319 | 3/2002 |
| WO | WO 02/33350 A | 4/2002 |
| WO | WO 03/068103 A | 8/2003 |

* cited by examiner

 
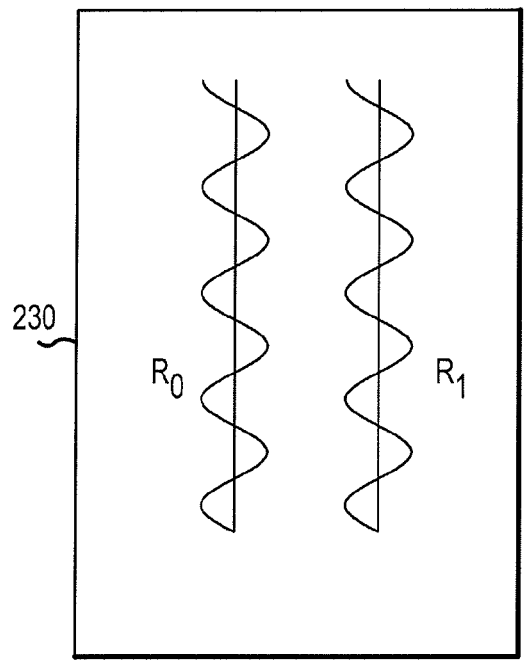 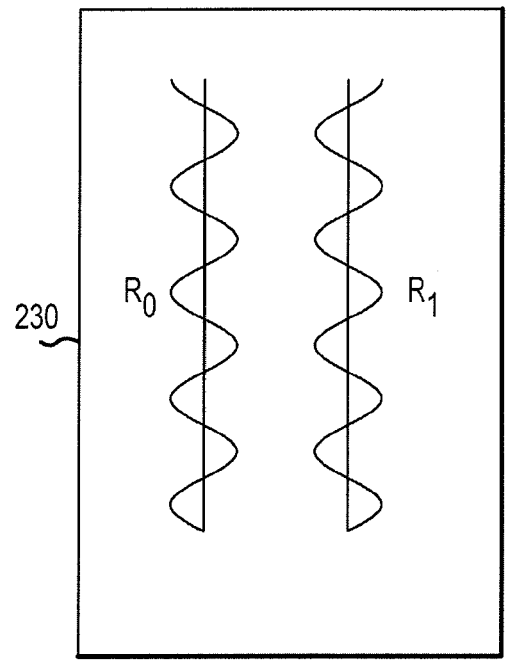
FIG.4A　　　　　　FIG.5A
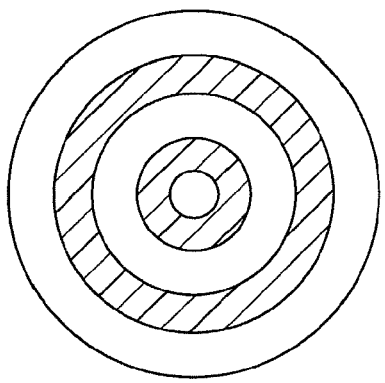 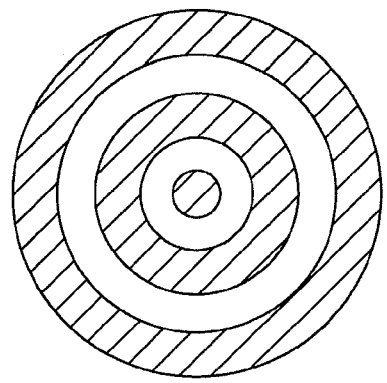
FIG.4B　　　　　　FIG.5B

SYSTEM AND METHOD FOR LASER ABLATION CALIBRATION

CROSS-REFERENCES TO RELATED APPLICATIONS

This application is related to U.S. Pat. Nos. 5,599,934, 6,195,164, 6,666,855, and to U.S. Patent Publication No. 2005/0215986, the entire disclosures of which are hereby incorporated by reference for all purposes.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

The present invention is directed to systems, methods, and apparatus for calibrating or verifying laser ablation systems. In particular, embodiments relate to methods and apparatus for measuring the refractive power, shape and quality of a laser test ablation on a test surface through interferometric techniques. Embodiments of the present invention are particularly useful for calibrating excimer lasers used during laser ablation procedures of the eye, such as photorefractive keratotomy (PRK), phototherapeutic keratectomy (PTK), laser in situ keratomileusis (LASIK), or the like.

Ultraviolet and infrared laser based systems and methods are known for enabling opthalmological surgery in order to correct vision defects and other precision structure modifications. These procedures generally employ an ultraviolet or infrared laser to remove a microscopic layer of an anterior stromal tissue from the cornea to alter its refractive power. In ultraviolet laser ablation procedures, the radiation ablates corneal tissue in a photodecomposition that does not cause thermal damage to adjacent and underlying tissue. Molecules at the irradiated surface are broken into smaller volatile fragments without substantially heating the remaining substrate; the mechanism of the ablation is photochemical, i.e. the direct breaking of intermolecular bonds. The ablation penetrates into the stroma of the cornea to change its contour for various purposes, such as correcting myopia, hyperopia, and astigmatism.

In such laser based systems and methods, the irradiated flux density and exposure of the cornea to the laser radiation are controlled so as to provide a surface sculpting of the cornea to achieve a desired ultimate surface change in the cornea. To that end, ablation algorithms have been developed that determine the approximate energy density that can be applied to remove a certain depth of tissue from the cornea. At ultraviolet wavelengths, for example, a cumulative energy density of about 1 Joule/$cm^2$ will typically ablate corneal tissue to a depth of about one micron when applied in a series of pulses of about 100 to 400 milliJoules/$cm^2$. Accordingly, the ablation algorithms are tailored for each procedure depending on the amount and the shape of corneal tissue which will be removed to correct a particular individual's refractive error.

In order to properly use these laser ablation algorithms, the laser ablation system typically should be calibrated. Calibration of the laser system helps ensure removal of the intended shape and quantity of the corneal tissue so as to provide the desired shape and refractive power modification to the patient's cornea. In addition, it is usually desirable to test for acceptable levels of system performance. For example, such tests can help ensure that internal optics are aligned, that laser fluence is accurate, that desired beam characteristics are maintained, and the like.

When performing laser eye surgery such as when ablating a target region on a patient's cornea with a refractive laser beam system, it is beneficial to have accurate information on the energy, dimensions, and other characteristics of the laser beam spot which is incident on the cornea in order to determine the best achievable surgical outcome. For calibration purposes, it is particularly useful to have detailed information regarding the pulse energy in order to ensure that the correct profile is ablated onto the patient's cornea.

Ablations of plastic test materials are often performed prior to excimer laser surgery. During these tests, a lens is ablated into the test plastic, and the refractive power of the test lens is read by a standard lensometer. The reading from the lensometer is then entered back into the laser system so that the system can make appropriate calibration adjustments. The test lens may also be visually evaluated under a magnifying glass or with the microscope of the laser system, and test samples are sometimes sent to a laboratory for accurate evaluation to help determine beam homogeneity and quality.

Although known laser ablation calibration techniques are effective, some methods still suffer from certain disadvantages. For example, delaying each surgery while obtaining accurate laboratory evaluations of a test lens may be impractical. Nonetheless, some information beyond refractive power and a visual evaluation of the test lens would be helpful to improve the accuracy of regular calibrations, whether they are performed monthly, daily, or before each ablation procedure.

In light of the above, it would be desirable to provide improved systems, methods, and apparatus for calibrating laser ablation procedures. It would be particularly desirable if such improvements enhanced calibration accuracy without significantly increasing the overall system costs and complexity. It would further be desirable if such improvements could provide quantifiable data which might be used in an automated calibration feedback and adjustment system.

BRIEF SUMMARY OF THE INVENTION

Embodiments of the present invention is directed to improved systems, methods, and apparatuses for calibrating a laser ablation system, such as an excimer laser system for selectively ablating the cornea of a patient's eye, based on optical measurement. Embodiments provide apparatus and methods for analyzing a test surface that has been or is being ablated by energy delivered from a laser, such as an excimer laser. In addition, embodiments provide apparatus and methods for monitoring system performance, such as inaccurate beam characteristics, flawed internal optics, misalignment, poor laser fluence, and the like. Conveniently, these approaches can use existing components of the laser ablation system such as a microscope, video camera, computer processor, and other system components. These improved calibration techniques allow enhanced quantitative evaluations of the test surface at low cost and with little delay, and can also be used to accurately and automatically adjust the laser system. The also provide for a reliable approach to monitoring the day to day performance of an ablation system.

In a first aspect, embodiments of the present invention provide a method of determining an ablation beam characteristic. The method can include ablating an article with the ablation beam so as to form a test location having an ablation depth, separating light from a light source into a first beam and a second beam, transmitting the first beam through the test location, transmitting the second beam through a reference location disposed outside of the ablation, and determining an ablation beam characteristic based on a phase relationship of the first beam and the second beam downstream of the article. In some cases, the method may include calibrating the ablation beam based on the ablation beam characteristic. The ablation beam characteristic can be based on a phase relationship of the first beam and the second beam at a target zone, where the target zone is disposed downstream of the article. In some embodiments, the ablation beam includes a pulsed ultraviolet laser, and the article includes a clear plastic. In some embodiments, the phase relationship is determined based on a superimposition of the first beam and the second beam at a target zone. The ablation depth of the test location can be determined based on the phase relationship, and the ablation beam characteristic can be determined based on the ablation depth. In some cases, the first beam is transmitted at a known phase relationship with the second beam. In some cases, the first beam is transmitted along a first beam path that travels through a transmission zone, through the test location, to the target zone, and the second beam is transmitted along a second beam path that travels through the transmission zone, through the reference location, to the target zone, and the ablation beam characteristic is determined based on a first beam phase at the transmission zone, a second beam phase at the transmission zone, and the phase relationship of the first beam and second beam at the target zone. In some embodiments, the first beam and the second beam both originate from a common input source beam. The ablation beam characteristic can include a member selected from the group consisting of an ablation beam pulse energy, an ablation beam pulse rate, an ablation beam cross-section, and an ablation beam energy distribution profile.

In another aspect, embodiments provide a system for determining an ablation beam characteristic. The system can include a light source assembly that transmits a first beam through a test location of an article and transmits a second beam through a reference location, such that the reference location is disposed outside of the test location. The test location is typically ablated by the ablation beam. The system can also include a sensor assembly that detects a first beam and second beam superimposition downstream of the article, a processor coupled with the sensor assembly, and a memory coupled with the processor. The memory can embody a phase relationship code module for determining a phase relationship between the first beam and the second beam, based on the first beam and second beam superimposition. In some embodiments, the system includes a calibration code module for determining a depth of the ablation beam based on the phase relationship. The light source assembly can be configured to transmit the first beam at a known phase relationship with the second beam. In some cases, the light source assembly can be configured to transmit the first beam from a transmission zone through the test location to a target zone, and to transmit the second beam from the transmission zone through the reference location to the target zone. The calibration code module can be configured to determine the depth of the ablation beam based on a first beam phase at the transmission zone, a second beam phase at the second transmission zone, and the phase relationship of the first beam and second beam at the target zone. In some embodiments, the light assembly includes a light source and a splitter that is configured to split a light beam from the light source into the first beam and the second beam. Calibration can include an adjustment of an ablation beam characteristic, where the ablation beam characteristic includes a member selected from the group consisting of an ablation beam pulse energy, an ablation beam pulse rate, an ablation beam cross-section, and an ablation beam energy distribution profile.

In another aspect, embodiments provide a method of calibrating an ablation beam. The method can include ablating a region of an article with the ablation beam, transmitting a first beam through the ablated region to a target zone, transmitting a second beam to the target zone outside of the ablated region, determining an ablation beam characteristic based on a phase relationship of the first beam and the second beam at the target zone, and calibrating the ablation beam based on the ablation beam characteristic.

BRIEF DESCRIPTION OF THE DRAWINGS

FIGS. 4A and 4B illustrate light beam constructive interference according to one embodiment of the present invention.

FIGS. 5A and 5B illustrate light beam destructive interference according to one embodiment of the present invention.

DETAILED DESCRIPTION OF THE INVENTION

Embodiments of the present invention provide systems, devices, and methods that can use superimposed light beams to calculate ablation beam characteristics such as ablation rate and beam profile. Embodiments also provide method and systems for optically measuring the ablation characteristics of a well defined test material. Embodiments of the present invention may be generally useful for enhancing the accuracy and efficacy of laser eye surgical procedures, such as photorefractive keratectomy (PRK), phototherapeutic keratectomy (PTK), laser in situ keratomileusis (LASIK), and the like. Embodiments can provide enhanced accuracy of ablative procedures by improving the methodology for calibrating or verifying laser ablation systems. In one particular embodiment, the present invention is related to therapeutic wavefront-based ablations for pathological eyes.

Embodiments of the present invention can be readily adapted for use with existing laser systems, wavefront measurement systems, and other optical measurement devices. While embodiments of the systems, software, and methods of the present invention are described primarily in the context of a laser eye surgery system, it should be understood that embodiments may be adapted for use in alternative eye treatment procedures and systems such as spectacle lenses, intraocular lenses, contact lenses, corneal ring implants, collagenous corneal tissue thermal remodeling, industrial laser processing of other materials, and the like.

Figure 1:
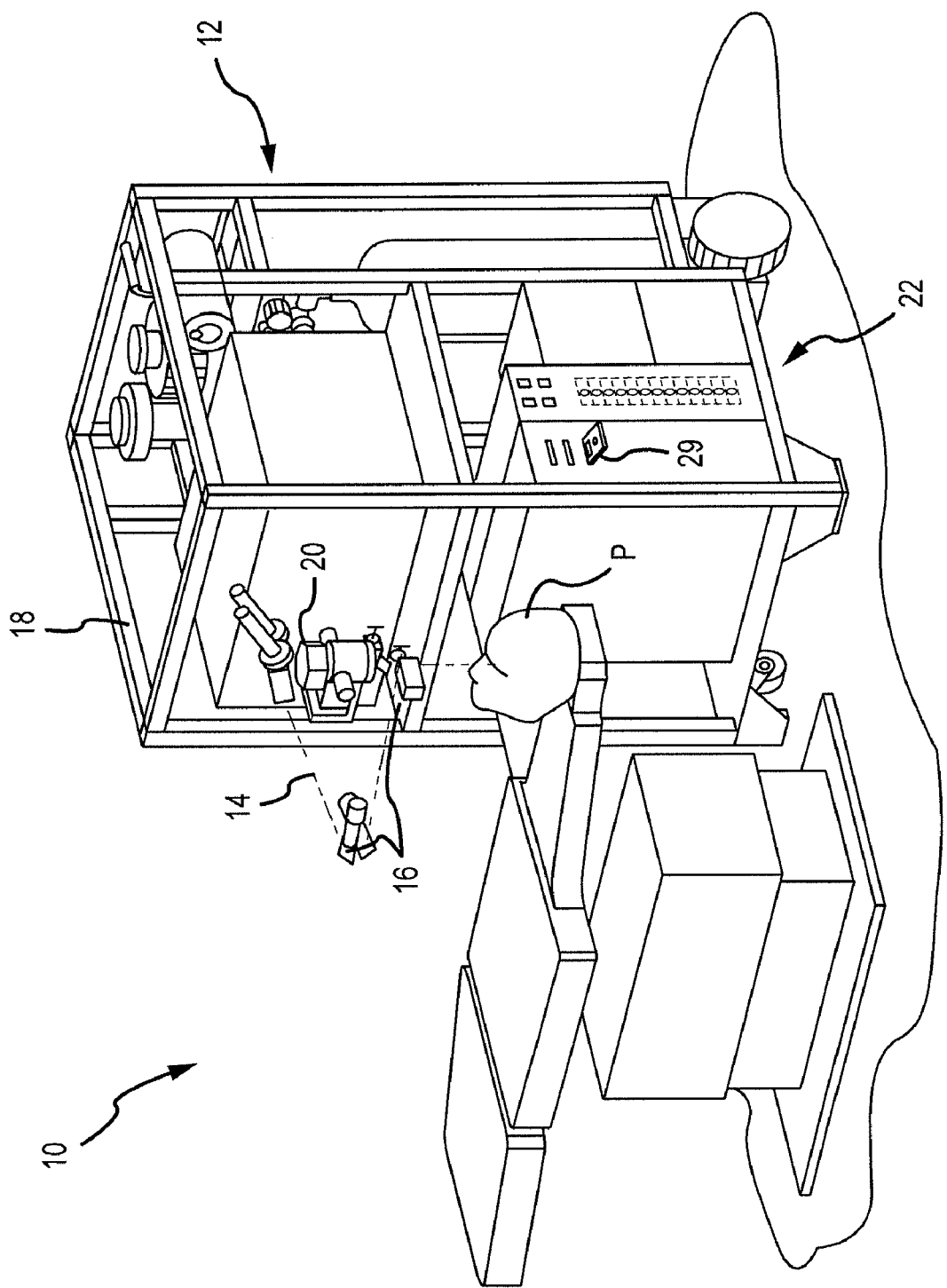
FIG. 1 illustrates a laser ablation system according to one embodiment of the present invention.

Referring now to FIG. 1, a laser eye surgery system 10 embodiment of the present invention includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. A microscope 20 is mounted on the delivery optics support structure, the microscope often being used to image a cornea of the eye.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via laser delivery optics 16. Alternative sources of ultraviolet or infrared radiation may also be used, particularly those adapted to controllably ablate the corneal tissue without causing significant damage to adjacent and/or underlying tissues of the eye. In alternate embodiments, the laser beam source employs a solid state laser source having a wavelength between 193 and 215 nm as described in U.S. Pat. Nos. 5,520,679, and 5,144,630 to Lin and U.S. Pat. No. 5,742,626 to Mead, the full disclosures of which are incorporated herein by reference. In another embodiment, the laser source is an infrared laser as described in U.S. Pat. Nos. 5,782,822 and 6,090,102 to Telfair, the full disclosures of which are incorporated herein by reference. Hence, although an excimer laser is the illustrative source of an ablating beam, other lasers may be used in embodiments of the present invention.

Laser 12 and laser delivery optics 16 will generally direct laser beam 14 to the eye of patient P under the direction of a computer system 22. Computer system 22 will often selectively adjust laser beam 14 to expose portions of the cornea to the pulses of laser energy so as to effect a predetermined sculpting of the cornea and alter the refractive characteristics of the eye. In many embodiments, both laser 12 and the laser delivery optical system 16 will be under control of computer system 22 to effect the desired laser sculpting process, with the computer system effecting (and optionally modifying) the pattern of laser pulses. The pattern of pulses may be summarized in machine readable data of tangible media 29 in the form of a treatment table, and the treatment table may be adjusted according to feedback input into computer system 22 from an automated image analysis system (or manually input into the processor by a system operator) in response to real-time feedback data provided from an ablation monitoring system feedback system. The laser treatment system 10, and computer system 22 may continue and/or terminate a sculpting treatment in response to the feedback, and may optionally also modify the planned sculpting based at least in part on the feedback.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like.

Figure 2:
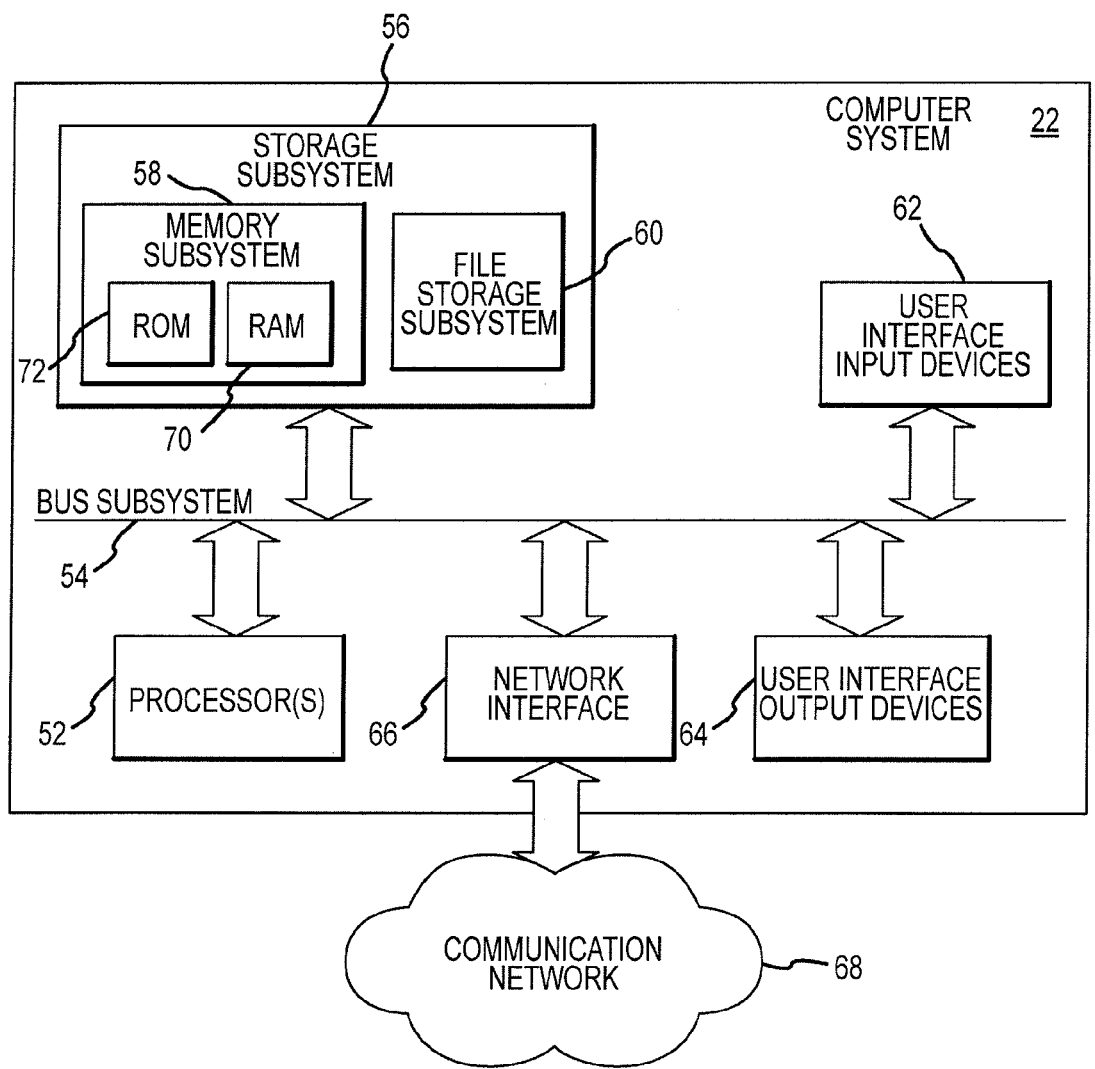
FIG. 2 illustrates a simplified computer system according to one embodiment of the present invention.

FIG. 2 is a simplified block diagram of an exemplary computer system 22 that may be used by the laser surgical system 10. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices.

Storage subsystem 56 stores the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Methods and apparatuses described herein can determine ablation beam characteristics such as the pulse energy of the beam incident upon the target. Accordingly, laser beam spot shape and intensity profiles can be generated for use in sculpting the patient's cornea with a pattern of laser beam spots thereon. By determining the exact intensity of the laser beam spot, a desired corneal ablation treatment can be effected without underablating intended targets, thereby enhancing the accuracy of the resculpting algorithm and procedure.

When targeting an excimer laser beam to ablate regions of a patient's cornea during laser eye surgery, the spot formed by the laser beam upon the target will often have a circular shape, and will typically be intended to have a substantially uniform energy distribution. Other known beam delivery systems have rectangular or slit-shaped beams, optionally with Gaussian or other uneven energy profiles. It is often beneficial to know the intensity and shape profile of the laser beam as accurately as possible, especially when generating a pattern of laser beam spot application to the patient's cornea. Having accurate intensity or shape profile for the laser beam spot, it is possible to accurately sculpt the patient's cornea through successive application of a laser beam in a pattern of spots on the cornea. Accurate determination of intensity or shape profiles of the laser beam spot can be used to generate targeting patterns, and to otherwise calibrate or validate the system. In some embodiments, calibration of the ablation system or beam can involve adjusting certain ablation system or beam parameters. In other embodiments, calibration of the ablation system or beam involve verifying or qualifying that certain ablation system or beam characteristics meet a specification.

Figure 3A:
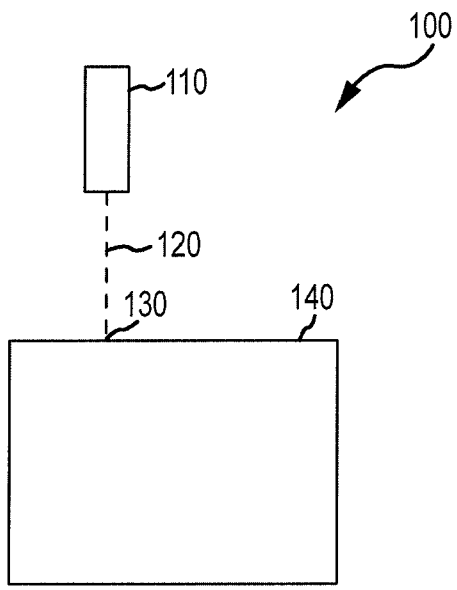
FIGS. 3A-3D illustrate aspects of a calibration system according to one embodiment of the present invention.

FIGS. 3A-3D illustrate various aspects of an embodiment according to the present invention. As seen in FIG. 3A, beam characterizing system 100 can include an ablation system 110. In some cases, ablation system 110 may include an excimer laser such as an argon-fluoride excimer laser producing laser energy with a wavelength of about 193 nm. Alternative laser systems may include solid state lasers, such as frequency multiplied solid state lasers, flash-lamp, and diode pumped solid state lasers, pulsed ultra-violet lasers, and the like. Exemplary solid state lasers include UV solid state lasers producing wavelengths of approximately 193-215 nm such as those disclosed in U.S. Pat. Nos. 5,144,630, and 5,742,626, and in Borsuztky et al., "Tunable UV Radiation at Short Wavelengths (188-240 nm) Generated by Frequency Mixing in Lithium Borate", Appl. Phys. 61:529-532 (1995). In some embodiments, a laser may emit at a target fluence of 160 mJ/cm$^2$. In related embodiments, an HeNe laser illuminating at a wavelength of 633 nm may be used. A variety of alternative lasers might also be used, for example homogeneous, Gaussian, or reverse Gaussian lasers. The laser energy will often comprise a beam formed as a series of discreet laser pulses or shots. Ablation system 110 can generate an ablation beam 120 which may be directed toward article 140 to create an ablation at test location 130 having an ablation depth. In some embodiments, ablated test location 130 is defined by the ablation, or vice versa. It is appreciated that embodiments contemplate the use of laser or ablation beam suitable for refractive correction or precision surface machining.

Figure 3B:
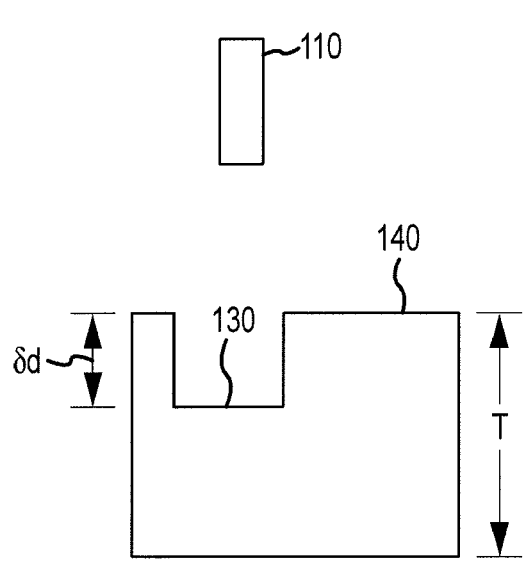

FIG. 3B illustrates test article 140 which is being or has been ablated according to an ablation protocol such that ablation or test location 130 is being or has been ablated to a depth of δd. Article 140 will typically include a polymer material of thickness T that can be ablated with an excimer laser in a repeatable, predictable manner. Suitable test ablation materials include clear plastic, polymethylmethacrylate ("PMMA"), and the like. Typically, article 140 will be ablated with ablation beam 120 which is the same as that applied to a patient's cornea during treatment. It is appreciated that embodiments of the present invention contemplate the use of any material 141 amenable to ablation and suitable for interferometric analysis. Often, such materials will exhibit a reproducible ablation rate, as well as a suitable ablation rate for the particular laser wavelength used.

Figure 3C:
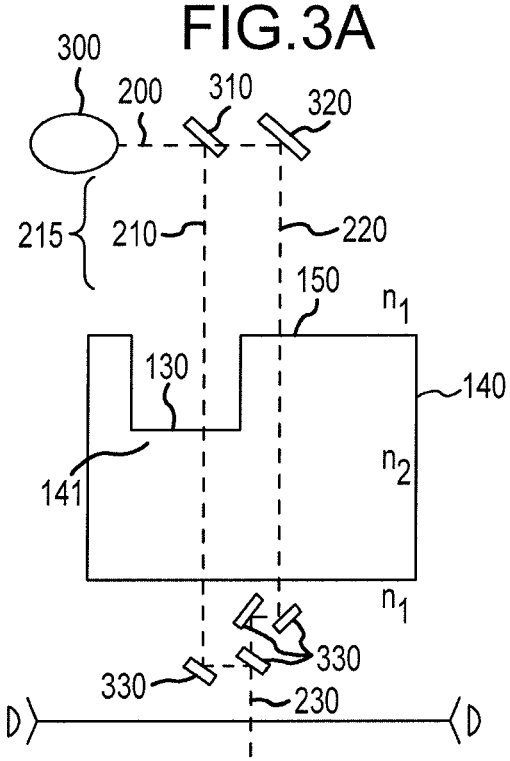

As seen in FIG. 3C, a coherent light beam 200 from a light source 300 or other common input source beam can be separated by a beam splitter 310 into a first beam 210 ($R_0$) and a second beam 220 ($R_1$) whereby first beam 210 and second beam 220 have a static phase relationship. First beam 210 and second beam 220 will usually have a known phase relationship regardless of source. Typically, coherent beams can be combined to produce an unmoving distribution of constructive and destructive interference, or a detectable interference pattern, depending on the relative phase of the beams at their meeting point. In contrast, beams that are incoherent, when combined, often produce rapidly moving areas of constructive and destructive interference and thus are not likely to produce a visible interference pattern. A beam can be coherent with itself, a property sometimes known as temporal coherence. If a beam is combined with a delayed copy of itself, the duration of the delay over which it produces visible interference may be known as the coherence time of the beam. The temporal coherence of a beam is often related to the spectral bandwidth of the beam source.

Light beams produced by a laser, a typically intense monochromatic beam of coherent light, often have high temporal and spatial coherence, although the degree of coherence may depend on the properties of the laser. For example, a stabilized helium-neon laser can produce light with coherence lengths in excess of 5 m. Coherent beams generally come from, or are phase-locked to, the same source, or may be monochromatic with the same frequency. For example, by using extremely stable oscillators, two or more different sources can be used to produce interference when there is a fixed phase relation between them (e.g. they are phase-locked). In such a case, the interference generated is the same as with a single source. In some cases, the beams may have known but different wavelengths, and/or known but different phases. Embodiments may use a light source suitable for interferometric analysis, with exemplary embodiments including a 633 nm HeNe light source, having a power in the range from between about 0.5 mw to about 50 mw.

In the embodiment shown here, beam splitter 310 directs first beam 210 toward test location 130, and a mirror 320 directs second beam 220 toward reference location 150 of article 140, where reference location 150 is located outside of ablation or test location 130. It is appreciated that in some embodiments, reference location 150 may be external to or otherwise independent of article 140, and in some cases may include a reference material or article that is independent from the ablated article. Each of beams 210 and 220 pass through transmission zone 215. Typically, the phase relationship between first beam 210 and second beam 220 as they pass through transmission zone 215, is known, and in the case of coherent light, beams 210 and 220 are usually in phase. Source 300 can be configured to delivery any of a variety of types of electromagnetic radiation. The refractive index of article 140 can be characterized as $n_2$, and the refractive index of the upstream and downstream media relative to article 140 or otherwise surrounding article 140 can be characterized as $n_1$. Typically, when light passes from a first medium into a second medium, the velocity of the light is altered proportional to the refractive index differences between the two media. In some embodiments, the refractive index can be defined as the factor by which the phase velocity of electromagnetic radiation is slowed relative to vacuum. Due to the ablation at test location 130, the amount of test article 140 material that first beam 210 passes through is less than the amount of test article 140 material that second beam 220 passes through.

Figure 3D:
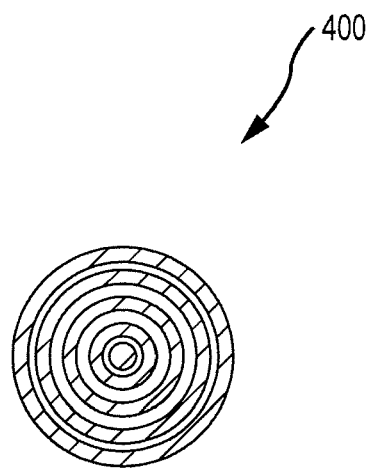

It is possible to combine first beam 210 and second beam 220, for example by using appropriately positioned mirrors 330, or a lens system having one or more lenses (not shown), or both, to produce a detectable interference pattern 400, or a distribution of constructive and destructive interference. In this manner, it is possible to probe even subwavelength details about article 140. FIG. 3D is an elevational view taken along a line D-D of FIG. 3C, illustrating interference pattern 400 created by first beam 210 and second beam 220 downstream of article 140, which may be, for example, at a target zone, or incident on a surface. Interference pattern 400 can be analyzed to determine a phase relationship between first beam 210 and second beam 220 downstream of article 140. As further discussed below, an ablation beam characteristic can be determined based on the phase relationship. Ablation system 110 can be calibrated or validated based on the ablation beam characteristic. In some embodiments, first beam 210 and second beam 220 may not be combined with mirrors 330 after passing through article 140, yet a resulting interference pattern produced by superposition of at least portions of the beams may be analyzed using standard interferometric techniques.

A wide variety of ablation beam characteristics can be measured and used to calibrate the ablation beam. For example, repetition rate or pulsing frequency usually relates to the number of pulses per second emitted from the laser, and is typically measured in Hertz (Hz). Pulse energy, measured in Joules, typically refers to the amount of energy in a laser pulse. Pulse duration or pulse width can refer to the time duration of the pulse, and is often measured in milliseconds.

Interference pattern characteristics resulting from the superimposition of first beam 210 and second beam 220 are further illustrated in schematic FIGS. 4A and 4B and FIGS. 5A and 5B. For the sake of illustration, first beam $R_0$ and second beam $R_1$ are shown as separate lines, although it is understood that the combined resulting beam 230 typically includes a superimposition of the beams. The relative phase of first beam $R_0$ and second beam $R_1$ depends in part on the depth of test location 130. In FIG. 4A, first beam $R_0$ and second beam $R_1$ are in phase. Consequently the constructive interference pattern, shown in FIG. 4B, which results from the superimposition of ($R_0+R_1$), has a bright spot in the center, and an alternating pattern of dark and bright rings, or fringes, expanding outward. In FIG. 5A, first beam $R_0$ and second beam $R_1$ are 180 degrees out of phase, and thus the interference pattern is different. The radii of the maxima in FIG. 4B occupy the radii of the minima in FIG. 5B. Consequently the destructive interference pattern, shown in FIG. 5B, which results from the superimposition of ($R_0+R_1$), has a dark spot in the center, and an alternating pattern of bright and dark rings, or fringes, expanding outward.

Figure 5C:
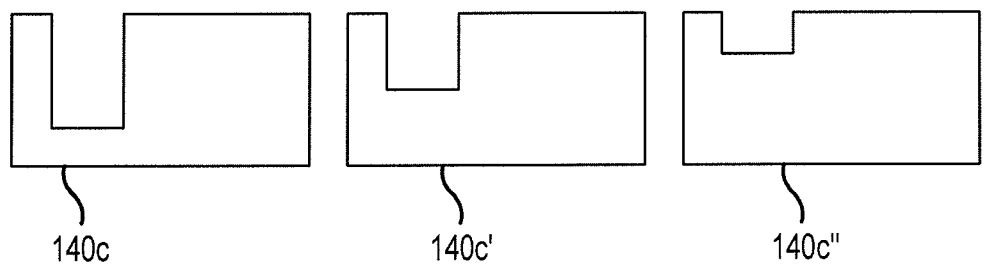
FIGS. 5C-5E illustrate articles according to various embodiments of the present invention.
Figure 5D:
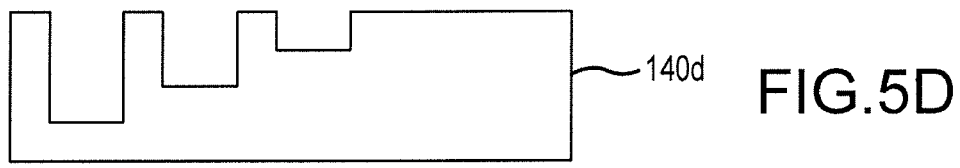
Figure 5E:
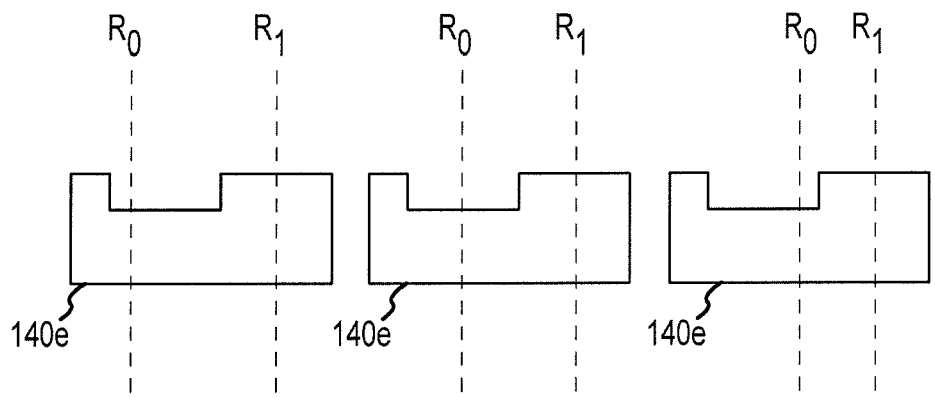

In practice, the phase relationship between first beam $R_0$ and second beam $R_1$ may fall somewhere along the spectrum between being completely in phase (FIGS. 4A and 4B) and 180 degrees out of phase (FIGS. 5A and 5B). For example, where first beam $R_0$ and second beam $R_1$ differ in phase by 10 degrees, the center spot in the interference pattern may be slightly darker than the center spot shown in FIG. 4B, yet lighter than a center spot in an interference pattern resulting from a first beam $R_0$ and second beam $R_1$ that differ in phase by 30 degrees. In some embodiments, as illustrated in FIG. 5C, a series of articles 140c, 140c', and 140c" having graduating test location depths, may be useful in establishing a baseline for carrying out certain embodiments of the calibration and validation steps discussed herein. Similarly, in some embodiments, as illustrated in FIG. 5D, a single article 140d having a series of graduating test location depths may be used in the calibration and validation techniques. In other embodiments, as illustrated in FIG. 5E, the methods and systems of the present invention may involve transmitting first beam $R_0$ through the ablation or test location of article 140e at a series of discrete points. In each case, transmitted first beam $R_0$ can be combined with second beam $R_1$ to create an interference pattern or superimposition, which can be analyzed to gather information about the thickness or article 140e at or near the discrete point at which $R_0$ passes through article 140e. In some embodiments, the interference pattern may be evaluated at a central spot to determine the ablation depth or rate. In related embodiments, a location in the interference pattern outside of a central spot, may be evaluated when making such determinations. An evaluated location may be any part or location on the interference pattern. In this way, a phase difference between a test beam and a reference beam may be evaluated by analyzing the interference pattern intensity.

Figure 5F:
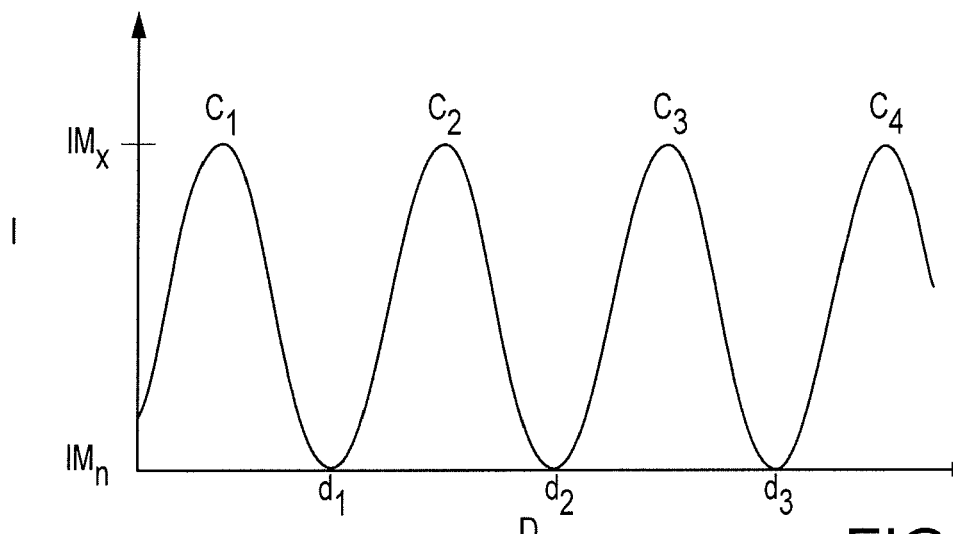
FIG. 5F illustrates a relationship between interference and ablation depth according to one embodiment of the present invention.

FIG. 5F graphically illustrates a relationship between interference (I) and accumulated ablation depth (D) according to one embodiment of the present invention. Starting at an ablation depth of zero, or any other desired starting ablation depth, as the ablation depth (D) increases, a series of constructive interference points ($c_1$, $c_2$, $c_3$, and $c_4$) can be observed at interference maximum (IMx), and a series of destructive interference points ($d_1$, $d_2$, and $d_3$) can be observed at interference minimum (IMn). This evolution of the interference pattern typically relates to a changing phase differential or relationship between a first beam and a second beam, which in some cases may be referred to as a test beam and a reference beam. As noted previously, measurement of interference patterns may take place during or in between ablation steps. In some embodiments, as the ablation depth increases, the observed interference maxima, minima, or other specified intensity value, may be counted to determine a corresponding accumulated ablation depth. Relatedly, if the ablation leads to a phase difference that is greater than $2\pi$, it may be useful to count the occurrences of intensity minima, maxima, or other selected intensity values, to aid in the determination of the ablation depth.

Figure 6:
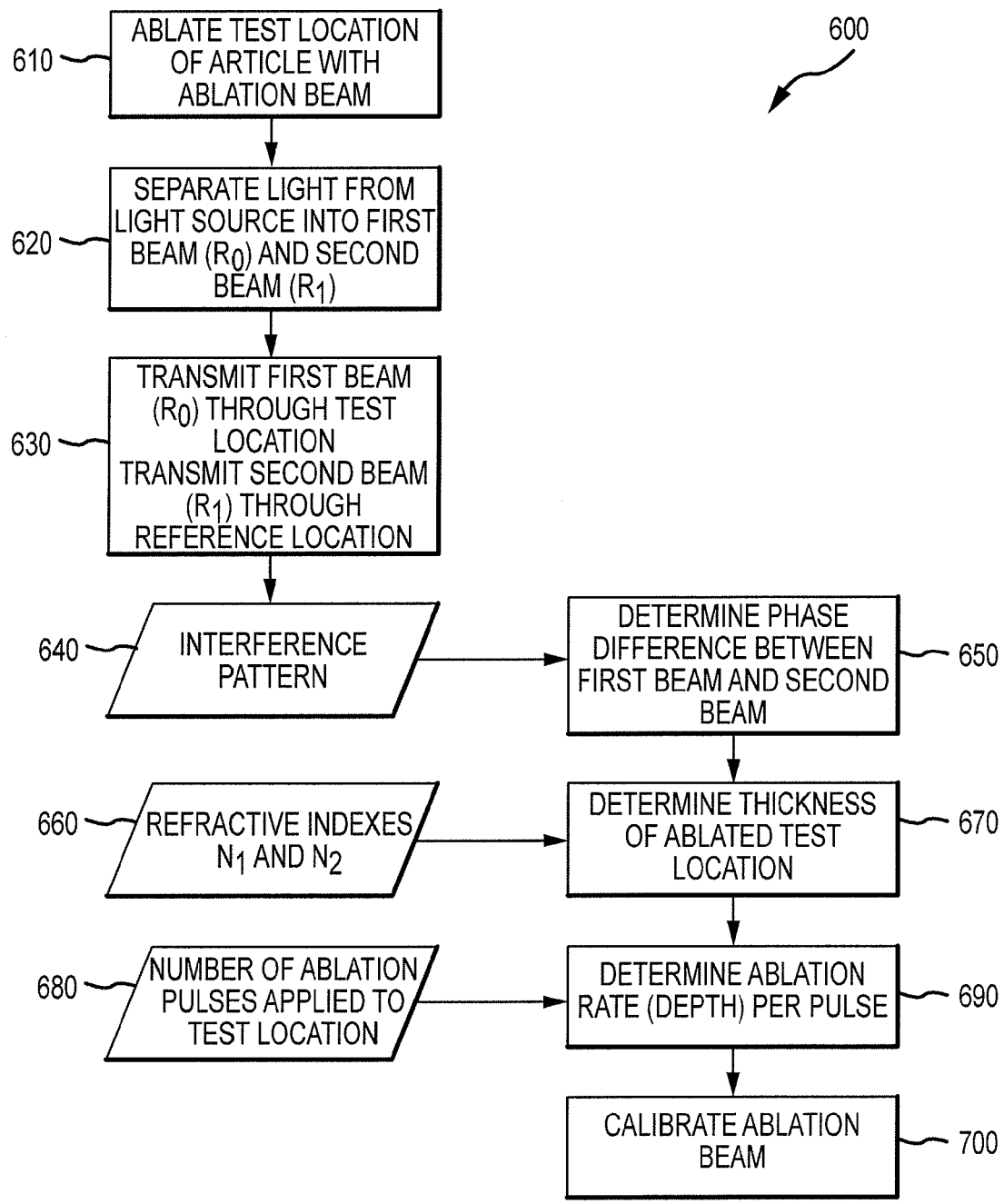
FIG. 6 illustrates an ablation beam calibration method according to one embodiment of the present invention.

As noted above, calibration of the ablation beam can optionally be based on an analysis of the interference pattern. FIG. 6 schematically illustrates an exemplary calibration method 600, certain steps of which can be performed by beam characterizing system 100 (e.g. FIGS. 4A-4D). Step 610 includes ablating a test location of an article with an ablation beam. Step 620 includes separating light from a light source into a first beam and a second beam. Step 630 includes transmitting the first beam through the test location, and transmitting the second beam through a reference location on the article that is outside of the test location. As a result of step 630, an interference pattern 640 can be created. Step 650 includes determining a phase difference or relationship between the first beam and the second beam, based on an analysis of interference pattern 640.

In many cases, the resulting interference pattern is recorded by a sensor assembly that includes a photodetector, a CCD video camera, or the like. In some cases, the resulting interference pattern may be analyzed via direct visual inspection. Other suitable means for evaluating the resulting interference pattern may be used.

In a fully constructive interference pattern (e.g. FIGS. 4A and 4B), the phase difference $\Delta\Phi$ between first beam 210 and second beam 220 is an integer multiple of wavelength. For example, $\Delta\Phi=m\lambda$, where m is an integer. For a fully destructive interference pattern (e.g. FIGS. 5A and 5B), the phase difference $\Delta\Phi$ between first beam 210 and second beam 220 is an odd-number multiple of half-wavelengths. For example, $\Delta\Phi=(m+1/2)\lambda$, where m is an integer.

Step 670 includes determining the thickness of the material that was ablated from the test location ($\delta d$), based on the phase difference and the refractive indexes $n_1$ and $n_2$. For example, $\Delta\Phi=(n_2-n_1)\Delta x$, where $\Delta\Phi$ represents the phase difference between first beam $R_0$ and second beam $R_1$. $\Delta x$ represents the thickness of the material that was ablated from the test location, and can also be expressed by the term $\delta d$. The refractive index of article 140 can be characterized as $n_2$, and the refractive index of the upstream and downstream media relative to article 140 or otherwise surrounding article 140 can be characterized as $n_1$.

Method embodiments of the present invention include determining an ablation beam characteristic such as ablation beam pulse energy, ablation beam pulse rate, ablation beam cross-section, and ablation beam energy distribution profile. Step 690 includes determining an ablation beam characteristic, specifically the ablation rate (depth) per pulse, based on the thickness of the material that was ablated from the test location ($\delta d$) and the number of ablation pulses applied to the test location. For example, if the thickness of the material that was ablated from the test location is 50 μm, and the number of applied ablation pulses is 534 pulses, then the ablation rate per pulse is 93 nm/pulse. This information can then be used to calibrate the ablation beam. For example, if an ablation rate per pulse greater than 93 nm/pulse is desired, the ablation rate per pulse can be adjusted upward. Similarly, if an ablation rate per pulse less than 93 nm/pulse is desired, the ablation rate per pulse can be adjusted downward.

In some embodiments, a calibration may be associated with a verification or qualification procedure. For example, an operator may ablate a test location of an article with a known number of pulses, and transmit a split source beam through the article as discussed elsewhere herein. If the intensity or brightness of a resulting interference spot is a certain value, or within an acceptable range, the operator may determine that the ablation beam is suitable for therapeutic use, thus verifying or qualifying the ablation system.

Figure 7:
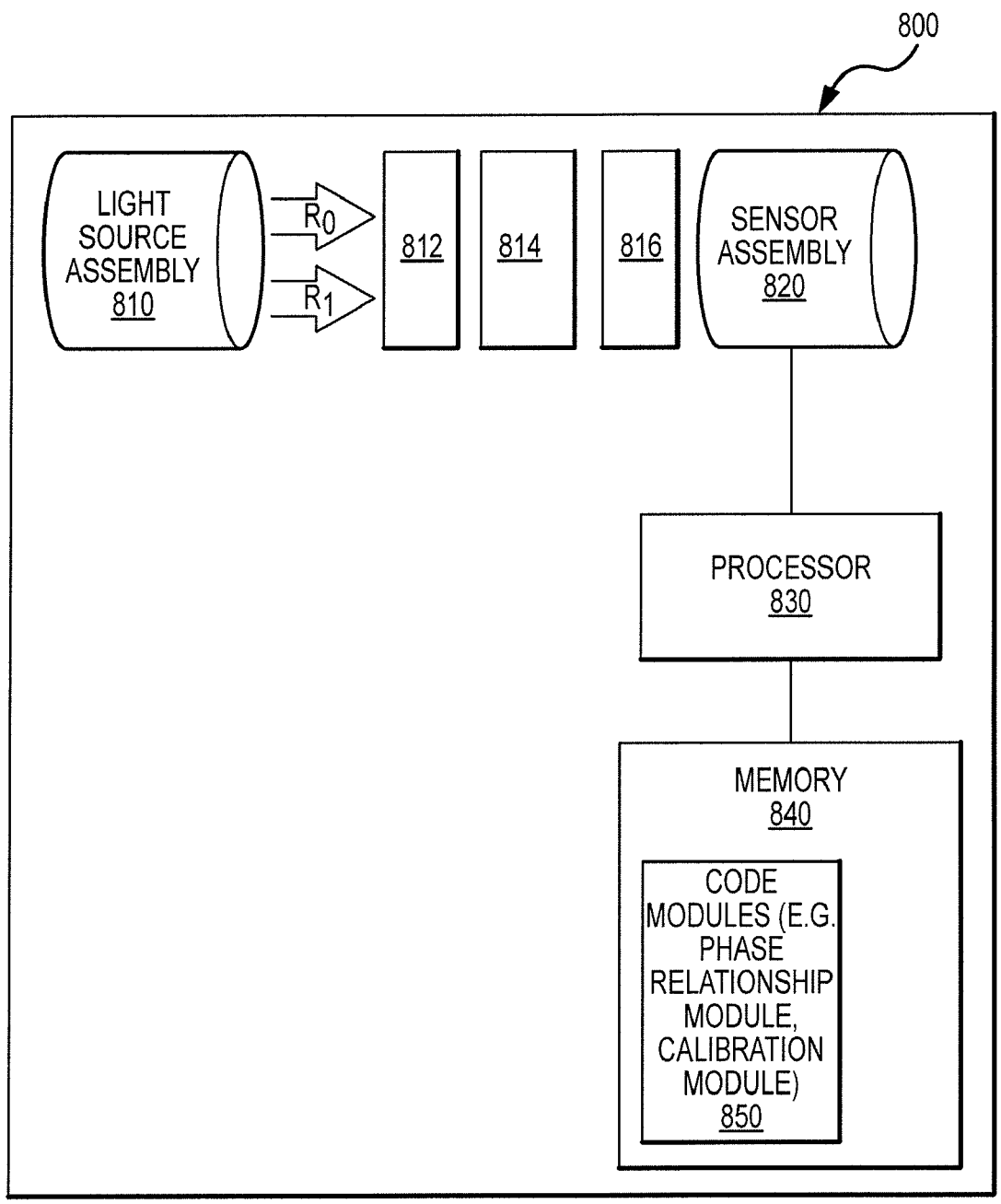
FIG. 7 illustrates a system for determining an ablation beam characteristic, according to one embodiment of the present invention.

FIG. 7 illustrates an embodiment of a system 800 for determining an ablation beam characteristic. System 800 can include a light source assembly 810 for transmitting a first beam through a test location of an article 814 and a second beam through a reference location on article 814, the reference location disposed outside of the test location, where the test location has been ablated by the ablation beam. System 800 can also include a sensor assembly 820 oriented for detecting a first beam and second beam superimposition downstream of article 814. System 800 can also include a processor 830 coupled with sensor assembly 820 and a memory 840 coupled with processor 830. Memory 840 can include or embody a plurality of code modules 850. Plurality of code modules 850 can include, for example, a phase relationship module for determining a phase relationship between the first beam and the second beam based on the first beam and second beam superimposition. In some embodiments, plurality of code modules 850 can include, a calibration module for determining a calibration for the ablation beam based on the phase relationship. It is appreciated that in some embodiments, light source assembly 810 can be configured to transmit the first beam at a known phase relationship with the second beam.

In some instances, light source assembly 810 may be configured to transmit the first beam from light source assembly 810, through a transmission zone 812, through the test location, and to a target zone 816. Similarly, light source assembly 810 may be configured to transmit the second beam from light source assembly 810, through transmission zone 812, through the reference location, and to target zone 816. The calibration module can be configured to determine the calibration based on a first beam phase at transmission zone 812, a second beam phase at transmission zone 812, and the phase relationship of the first beam and second beam at target zone 816. Calibration can include adjustment of an ablation beam characteristic, for example an ablation beam pulse energy, an ablation beam pulse rate, an ablation beam cross-section, an ablation beam energy distribution profile, and the like. Calibration can also involve verification or qualification of such ablation beam characteristics. In some cases, system 800 will be used in conjunction with a laser ablation system.

Each of the calculations described herein may be performed using a computer or other processor of laser system 10, of a wavefront sensor system or other opthalmological device, a stand-along general purpose computer, or the like, having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

A variety of modifications are possible within the scope of the present invention. For example, these techniques may be used to analyze a variety of radiation beams such as ultraviolet, gamma, and x-ray beams. The invention might be used with a wide variety of ablation planning protocols or algorithms, and provides input to such algorithms which can enhance their accuracy. A variety of parameters, variables, factors, and the like can be incorporated into the exemplary method steps or system modules. While the specific embodiments have been described in some detail, by way of example and for clarity of understanding, a variety of adaptations, changes, and modifications will be obvious to those of skill in the art. Treatments that may benefit from the invention include intraocular lenses, contact lenses, spectacles and other surgical methods in addition to refractive laser corneal surgery. Therefore, the scope of the present invention is limited solely by the appended claims.

What is claimed is:

1. A method of calibrating an ablation system that generates an ablation beam, the method comprising:
    ablating an article with the ablation beam generated by the ablation system so as to form a test location having an ablation depth, wherein the article comprises a test article material;
    separating light from a light source into a first beam and a second beam;
    transmitting the first beam through a first thickness of test article material at the test location while transmitting the second beam through a second thickness of test article material at a reference location, the reference location disposed outside of the test location and the first thickness different from the second thickness;
    determining an ablation beam characteristic based on a phase relationship of the transmitted first beam and the transmitted second beam; and
    calibrating the ablation system based on the determined ablation beam characteristic.

2. The method of claim 1, wherein the ablation beam characteristic is based on a phase relationship of the transmitted first beam and the transmitted second beam at a target zone.

3. The method of claim 1, wherein the ablation beam comprises a pulsed ultraviolet laser.

4. The method of claim 1, wherein the article comprises a clear plastic.

5. The method of claim 1, wherein the phase relationship is determined based on a superimposition of the first beam and the second beam at a target zone.

6. The method of claim 1, wherein the ablation depth of the test location is determined based on the phase relationship, and the ablation beam characteristic is determined based on the ablation depth.

7. The method of claim 1, wherein the first beam is transmitted at a known phase relationship with the second beam.

8. The method of claim 1, wherein the first beam is transmitted along a first beam path that travels through a transmission zone, through the test location, to the target zone, the second beam is transmitted along a second beam path that travels through the transmission zone, through the reference location, to the target zone, and the ablation beam characteristic is determined based on a first beam phase at the transmission zone, a second beam phase at the transmission zone, and the phase relationship of the first beam and second beam at the target zone.

9. The method of claim 1, wherein the article comprises the reference location, wherein the first beam and the second beam both originate from a common input source beam and impinge the article and emerge from the article as separated beams, and wherein the method further comprises superimposing the first beam and the second beam.

10. The method of claim 1, wherein the ablation beam characteristic comprises a member selected from the group consisting of an ablation beam pulse energy, an ablation beam pulse rate, an ablation beam cross-section, and an ablation beam energy distribution profile.

11. A system for calibrating an ablation beam, the system comprising:
    an article having a test location and a reference location and comprising a test article material, wherein the test location has been ablated by the ablation beam;
    a light source assembly configured to transmit a first beam through a first thickness of test article material at the test location of the article and a second beam through a second thickness of the test article material at the reference location, the reference location disposed outside of the test location and the first thickness different from the second thickness;
    a sensor assembly configured to detect a superimposition of the transmitted first beam and the transmitted second beam;
    a processor coupled with the sensor assembly; and
    a memory coupled with the processor, the memory embodying a phase relationship code module for determining a phase relationship between the first beam and the second beam, based on the first beam and second beam superimposition.

12. The system according to claim 11, the memory further comprising a calibration code module for determining a depth of the ablation beam based on the phase relationship.

13. The system according to claim 11, wherein the article comprises a clear plastic.

14. The system according to claim 11, wherein the light source assembly is configured to transmit the first beam at a known phase relationship with the second beam.

15. The system according to claim 11, wherein the light source assembly is configured to transmit the first beam from a transmission zone through the test location to a target zone, and the second beam from the transmission zone through the reference location to the target zone, and the calibration code module is configured to determine the depth of the ablation beam based on a first beam phase at the transmission zone, a second beam phase at the transmission zone, and the phase relationship of the first beam and second beam at the target zone.

16. The system according to claim 11, wherein the light assembly comprises a light source and a splitter configured to split a light beam from the light source into the first beam and the second beam.

17. The system according to claim 11, wherein the calibration comprises an adjustment of an ablation beam characteristic, the ablation beam characteristic comprising a member selected from the group consisting of an ablation beam pulse energy, an ablation beam pulse rate, an ablation beam cross-section, and an ablation beam energy distribution profile.

18. A method of calibrating an ablation beam, the method comprising:
    ablating a region of an article with the ablation beam, wherein the article comprises a test article material;
    transmitting a first beam through a first thickness of the test article material at the ablated region to a target zone while transmitting a second beam through a second thickness of the test article material to the target zone outside of the ablated region;
    determining an ablation beam characteristic based on a phase relationship of the transmitted first beam and the transmitted second beam at the target zone; and
    calibrating the ablation beam based on the ablation beam characteristic.

19. The method of claim 18, wherein the ablation beam comprises a pulsed ultraviolet laser.

\* \* \* \* \*